(12) United States Patent
Lu

(10) Patent No.: US 10,639,587 B2
(45) Date of Patent: May 5, 2020

(54) EXHAUST PURIFICATION SYSTEM

(71) Applicants: Shun-Tsung Lu, Taichung (TW);
Ta-Wei Lu, Taichung (TW)

(72) Inventor: Shun-Tsung Lu, Taichung (TW)

(73) Assignee: Shun-Tsung Lu, Taichung (TW)

( * ) Notice: Subject to any disclaimer, the term of this patent is extended or adjusted under 35 U.S.C. 154(b) by 232 days.

(21) Appl. No.: 15/891,319

(22) Filed: Feb. 7, 2018

(65) Prior Publication Data

US 2019/0240618 A1 Aug. 8, 2019

(51) Int. Cl.
*B01D 53/78* (2006.01)
*B01D 53/75* (2006.01)
*B01D 50/00* (2006.01)
*B01D 46/00* (2006.01)
*B01D 53/66* (2006.01)
*B01D 53/38* (2006.01)
*C02F 1/78* (2006.01)
*B01D 53/46* (2006.01)
*A61L 9/14* (2006.01)
*C02F 1/38* (2006.01)
*B01D 45/12* (2006.01)

(52) U.S. Cl.
CPC ............. *B01D 53/78* (2013.01); *A61L 9/14* (2013.01); *B01D 46/0073* (2013.01); *B01D 50/006* (2013.01); *B01D 53/38* (2013.01); *B01D 53/46* (2013.01); *B01D 53/66* (2013.01); *B01D 53/75* (2013.01); *C02F 1/78* (2013.01); *B01D 45/12* (2013.01); *B01D 2247/10* (2013.01); *B01D 2251/104* (2013.01); *B01D 2257/91* (2013.01); *B01D 2258/06* (2013.01); *B01D 2273/30* (2013.01); *C02F 1/38* (2013.01); *C02F 2301/026* (2013.01)

(58) Field of Classification Search
None
See application file for complete search history.

(56) References Cited

U.S. PATENT DOCUMENTS

| 3,625,883 | A | * | 12/1971 | Valdespino | ............... | C02F 9/00 |
| | | | | | | 210/754 |
| 3,658,249 | A | * | 4/1972 | Sharpe | ...................... | F02C 7/22 |
| | | | | | | 239/125 |
| 3,864,256 | A | * | 2/1975 | Hultsch | .................. | B01D 33/11 |
| | | | | | | 210/781 |

(Continued)

*Primary Examiner* — Amber R Orlando
*Assistant Examiner* — Phillip Y Shao
(74) *Attorney, Agent, or Firm* — Marshall A. Lerner; Bradford E. Mattes; Kleinberg & Lerner, LLP.

(57) ABSTRACT

An exhaust purification system has a centrifuge filter, a first fan device, a second fan device, a pump, and an ozone generator. The centrifuge filter has a container having a waste gas treating area and a wastewater treating area. The first fan device communicates with and draws gas into the waste gas treating area. The second fan device communicates with and draws the gas out of the waste gas treating area. The pump communicates with and draws wastewater from the wastewater treating area. The ozone generator communicates with the pump and introduces ozone into the wastewater inside the pump. A part of the ozone dissolved in the wastewater is released to the waste gas treating area to react with the gas, and the other part of the ozone dissolved in the wastewater reacts with the wastewater.

8 Claims, 3 Drawing Sheets

(56) References Cited

U.S. PATENT DOCUMENTS

| | | | |
|---|---|---|---|
| 4,655,932 A * | 4/1987 | Roslonski | C02F 11/121 |
| | | | 110/219 |
| 6,551,518 B2 * | 4/2003 | Gargas | C02F 1/4674 |
| | | | 205/752 |
| 7,481,935 B2 * | 1/2009 | Olivier | C02F 3/00 |
| | | | 210/620 |
| 9,993,745 B2 * | 6/2018 | Penny | B01D 17/047 |
| 2013/0098836 A1 * | 4/2013 | Penny | B01D 17/10 |
| | | | 210/601 |
| 2017/0166496 A1 * | 6/2017 | Imagawa | C01B 3/0015 |

* cited by examiner

US 10,639,587 B2

EXHAUST PURIFICATION SYSTEM

BACKGROUND OF THE INVENTION

1. Field of the Invention

The present invention relates to a purification system, and more particularly to an exhaust purification system that is capable of treating waste gas and wastewater simultaneously.

2. Description of Related Art

Since the industrial revolution taking place in the Great Britain in the 18th century, people have been benefited by massive production by machines. However, waste gas and wastewater produced from massive production continually damage the environment. In order to mitigate environmental damages caused by discharging the waste gas and the wastewater directly from factories, the factories are often equipped with an exhaust gas purification system or a wastewater purification system separately for treating waste gas or wastewater in advance before the waste gas and the wastewater are directly discharged from the factories.

However, the conventional purification system can treat either waste gas or wastewater. Once the factories have requirements of both waste gas and wastewater treatment, the factories have to be equipped with two purification systems, which causes poor space efficiency and raises cost of purchasing instruments.

To overcome the shortcomings of the conventional purification system, the present invention provides an exhaust purification system to mitigate or obviate the aforementioned problems.

SUMMARY OF THE INVENTION

The main objective of the present invention is to provide an exhaust purification system that is capable of treating waste gas and wastewater simultaneously, and may promote space efficiency and reduce cost for purchasing instruments.

The exhaust purification system comprises a centrifuge filter, a first fan device, a second fan device, a pump, and an ozone generator. The centrifuge filter has a container having a waste gas treating area and a wastewater treating area. The first fan device communicates with the waste gas treating area and draws gas into the waste gas treating area. The second fan device communicates with the waste gas treating area and draws the gas out of the waste gas treating area. The pump communicates with the wastewater treating area and draws wastewater into the wastewater treating area. The ozone generator communicates with the pump and introduces ozone into the wastewater inside the pump. A part of the ozone dissolved in the wastewater is released to the waste gas treating area to react with the gas, and the other part of the ozone dissolved in the wastewater reacts with the wastewater.

Other objects, advantages, and novel features of the invention will become more apparent from the following detailed description when taken in conjunction with the accompanying drawings.

DETAILED DESCRIPTION OF PREFERRED EMBODIMENTS

Figure 1:
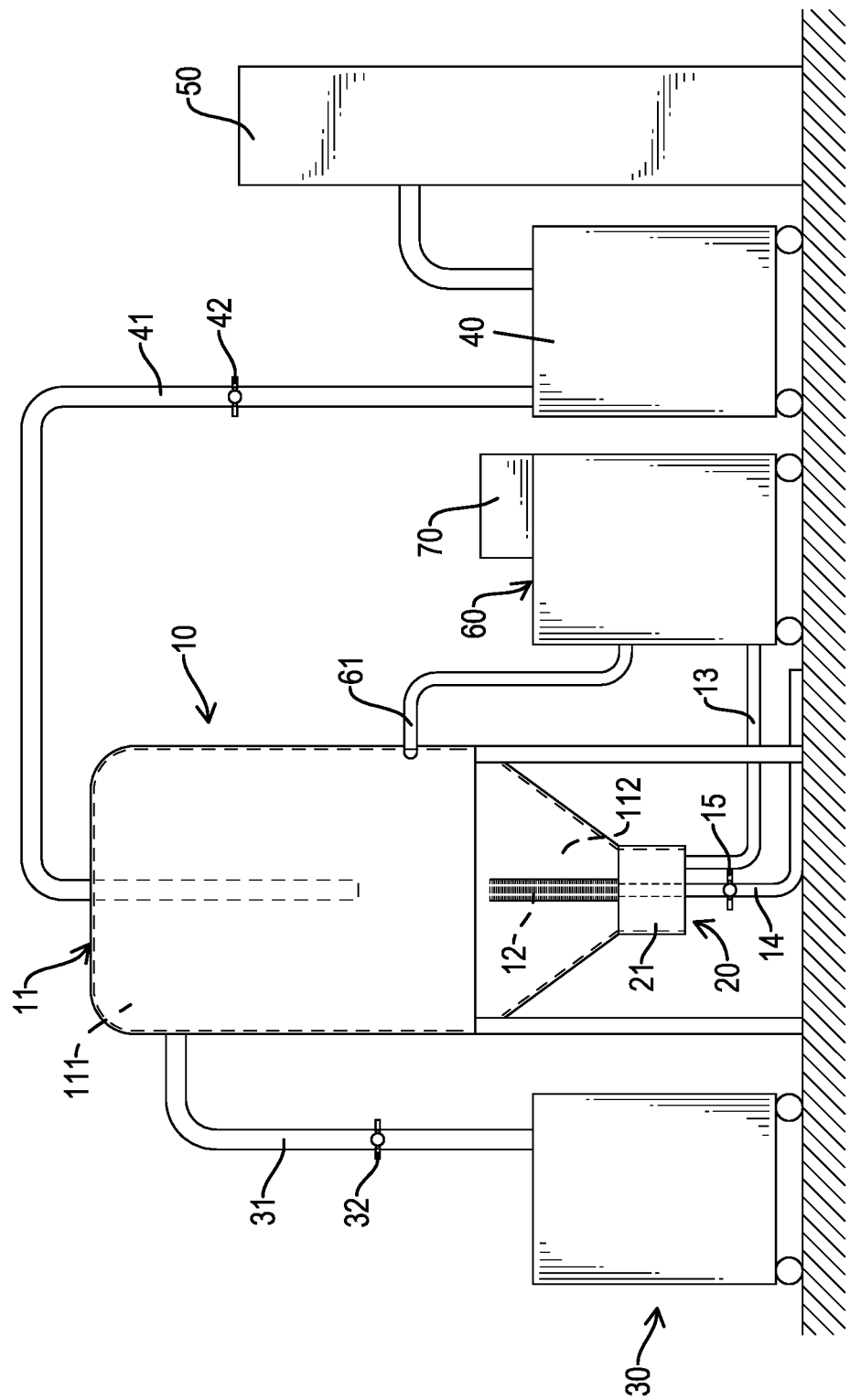
FIG. 1 is a side view of an exhaust purification system in accordance with the present invention.

With reference to FIG. 1, an exhaust purification system in accordance with the present invention has a centrifuge filter 10, an impurity discharging device 20, a first fan device 30, a second fan device 40, a chimney 50, a pump 60, and an ozone generator 70.

With reference to FIG. 1, the centrifuge filter 10 has a container 11, a spring 12, a return line 13, a discharge line 14, and a switch 15. The container 11 has a waste gas treating area 111 and a wastewater treating area 112 within the container 11. In the embodiment of the present invention, the container 11 has a peripheral wall. The peripheral wall of the container 11 has a circular cross section. The spring 12 is assembled inside the container 11 and is disposed in the wastewater treating area 112. The return line 13 has two opposite ends. One of the two opposite ends of the return line 13 is connected to the container 11. The return line 13 communicates with the wastewater treating area 112 of the container 11. The discharge line 14 has two opposite ends. One of the two opposite ends of the discharge line 14 is connected to the container 11. The discharge line 14 communicates with the wastewater treating area 112. The switch 15 is assembled to the discharge line 14 between the two opposite ends of the discharge line 14.

With reference to FIG. 1, the impurity discharging device 20 is connected to the container 11 of the centrifuge filter 10 and has an impurity receiver 21. An interior of the impurity receiver 21 communicates with the wastewater treating area 112 of the container 11.

With reference to FIG. 1, the first fan device 30 has an interior, a first linkage pipe 31, and an inlet adjusting valve 32. The first linkage pipe 31 communicates with the interior of the first fan device 30 and the waste gas treating area 111 of the container 11. The inlet adjusting valve 32 is assembled to the first linkage pipe 31.

With reference to FIG. 1, the second fan device 40 has an interior, a second linkage pipe 41, and a discharge adjusting valve 42. The second linkage pipe 41 communicates with the interior of the second fan device 40 and the waste gas treating area 111 of the container 11. The discharge adjusting valve 42 is assembled to the second linkage pipe 41.

With reference to FIG. 1, an interior of the chimney 50 communicates with the interior of the second fan device 40.

With reference to FIG. 1, the pump 60 has an interior and an inlet pipe 61. The inlet pipe 61 communicates with the interior of the pump 60 and the wastewater treating area 112 of the container 11. In the embodiment of the present invention, the inlet pipe 61 is connected to the container 11 and is tangent to the circular cross section of the container 11. The other one of the two opposite ends of the return line 13 is connected to the pump 60, and the return line 13 communicates with the wastewater treating area 112 of the container 11 and the interior of the pump 60.

With reference to FIG. 1, the ozone generator 70 is connected to the pump 60 and communicates with the interior of the pump 60.

Figure 3:
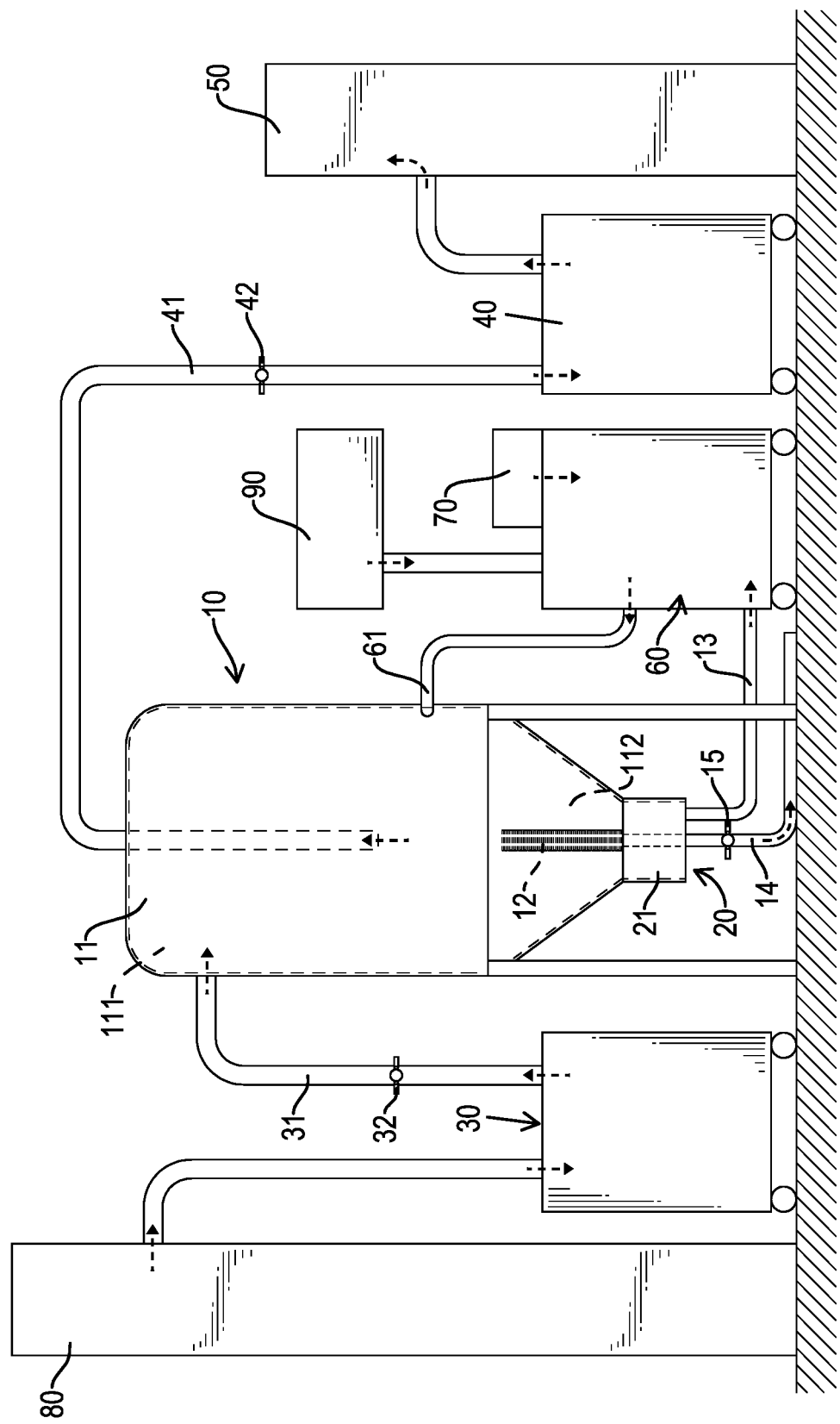
FIG. 3 is a schematic side view of the exhaust purification system in FIG. 1; showing waste gas and wastewater flowing.

With reference to FIG. 3, in use, the first fan device 30 communicates with a waste gas resource 80, and the pump 60 communicates with a wastewater resource 90. The pump 60 draws wastewater from the wastewater resource 90. The ozone generator 70 introduces ozone into the pump 60 and the ozone is dissolved in the wastewater inside the pump 60. The pump 60 injects both the wastewater and the ozone dissolved in the wastewater into the container 11 of the centrifuge filter 10. Meanwhile, the first fan device 30 draws waste gas from the waste gas resource 80 and injects the waste gas into the waste gas treating area 111 of the container 11. In the embodiment of the present invention, the wastewater and the ozone dissolved in the wastewater are disposed in the wastewater treating area 112 that is located at a lower portion of the container 11. The waste gas introduced into the container 11 of the centrifuge filter 10 is disposed in the waster gas treating area 112 that is located at an upper portion of the container 11.

Figure 2:
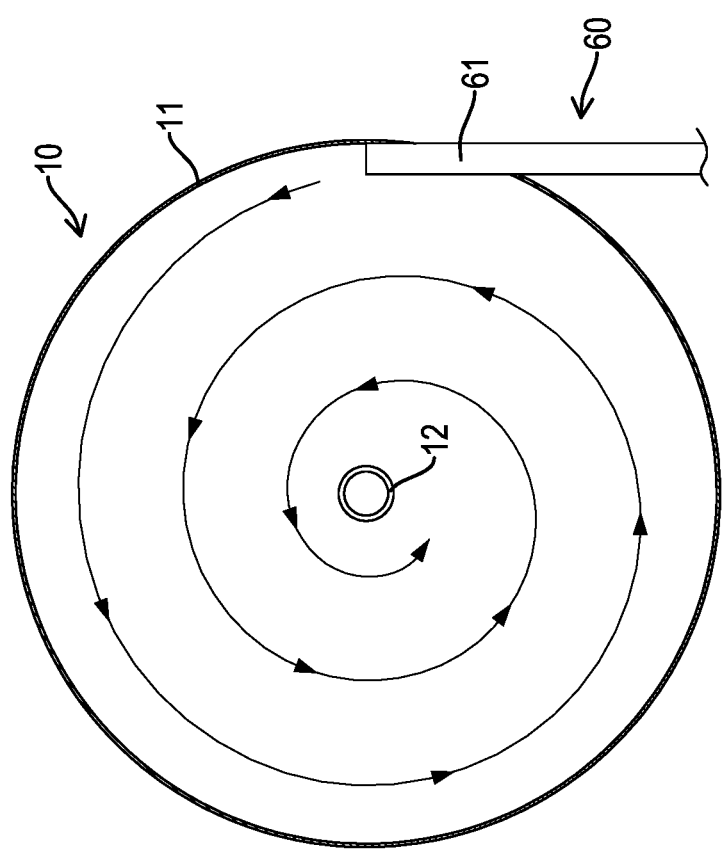
FIG. 2 is a schematic cross sectional side view of a container of a centrifuge filter of the exhaust purification system in FIG. 1.

When the wastewater and the ozone dissolved in the wastewater are introduced into the container 11 of the centrifuge filter 10 at the same time, a part of the ozone is released from the swirled wastewater. With reference to FIG. 2, in the embodiment of the present invention, since the peripheral wall of the container 11 has the circular cross section, the wastewater and the ozone dissolved in the wastewater are tangentially injected into the wastewater treating area 112 of the container 11 and are swirled along the peripheral wall of the container 11. The wastewater is swirled, gradually forms a vortex, and makes the ozone released from the wastewater rapidly. A part of the ozone is released from the wastewater and into the waste gas treating area 111 of the container 11 to react with the waste gas chemically. The other part of the ozone that is still dissolved in the wastewater reacts with the wastewater chemically. The ozone has an intensive oxidative capacity and is able to directly oxidize bacteria or virus. The ozone damages deoxyribonucleic acid, DNA of the bacteria or ribonucleic acid of virus to eliminate bacteria or virus inside the wastewater or waste gas.

The ozone is also able to remove toxic substance or odor substance inside the wastewater or waste gas. The ozone with the intensive oxidative capacity destructs chemical bonds of toxic substance or odor substance and turns the toxic substance or the odor substance into other substances with reduced toxicity or odor.

With reference to FIG. 3, when the wastewater passes through the spring 12 of the centrifuge filter 10, impurity inside the wastewater is filtrated by the spring 12, and the wastewater turns into purified water. When the switch 15 of the centrifuge filter 10 is turned on, the purified water is discharged via the discharge line 14. When the switch 15 is turned off, the purified water enters the pump 60 via the return line 13 for next treatment. On the other hand, the waste gas reacts with the ozone and turns into reacted gas inside the waste gas treating area 111 of the container 11. The second fan device 40 is turned on and draws reacted gas inside the second fan device 40 and the chimney 50 via the second linkage pipe 41. Then, the reacted gas is discharged from the chimney 50. Gas as waste gas and reacted gas flows through the waste gas resource 80, the first fan device 30, the container 11, the second fan device 40, and is eventually discharged from the chimney 50.

With reference to FIG. 3, the inlet adjusting valve 32 of the first fan device 30 and the discharge adjusting valve 42 are operated to adjust pneumatic pressure inside the first linkage pipe 31 of the first fan device 30 and the second linkage pipe 41 of the second fan device 40. The inlet adjusting valve 32 and the discharge adjusting valve 42 are able to control time that the waste gas stays in the waste gas treating area 111 of the container 11 and time that the waste gas reacts with the ozone.

The exhaust purification system in accordance with the present invention has the first fan device 30, the second fan device 40, and the pump 60. The first fan device 30, the second fan device 40, and the pump 60 communicate with the container 11 of the centrifuge filter 10 and are able to draw the waste gas and the wastewater into the container 11 respectively from the waste gas resource 80 and the wastewater resource 90 at the same time. The exhaust purification system in accordance with the present invention keeps the waste gas and the wastewater respectively within the waste gas treating area 111 and the wastewater treating area 112 to react with the ozone simultaneously. Compared to the conventional exhaust gas purification system or the conventional wastewater purification system, the exhaust purification system in accordance with the present invention is capable of treating both waste gas and wastewater at the same time to make a factory free from settling two purification systems and promotes space efficiency and lowers cost for purchasing purification systems. Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An exhaust purification system comprising:
   a centrifuge filter having
      a container having
         a waste gas treating area and a wastewater treating area;
      a first fan device having an interior communicating with the waste gas treating area of the container and drawing gas into the waste gas treating area;
      a second fan device having an interior communicating with the waste gas treating area of the container and drawing the gas out of the waste gas treating area;
      a chimney communicating with the second fan device and discharging the gas introduced from the waste gas treating area of the container;
      a pump having an interior communicating with the wastewater treating area of the container and drawing wastewater into the wastewater treating area of the container; and
      an ozone generator communicating with the interior of the pump and introducing ozone into the wastewater drawn by the pump, and the ozone dissolved in the wastewater drawn by the pump;
      wherein after the wastewater and the ozone introduced by the ozone generator and dissolved in the wastewater are introduced in the wastewater treating area of the container, a part of the ozone dissolved in the wastewater is released to the waste gas treating area to react with the gas inside the waste gas treating area, and the other part of the ozone dissolved in the wastewater reacts with the wastewater inside the wastewater treating area.

2. The exhaust purification system as claimed in claim 1, wherein
   the first fan device has
      a first linkage pipe communicating with the interior of the first fan device and the waste gas treating area of the container; and an inlet adjusting valve assembled to the first linkage pipe; and the second fan device has a second linkage pipe communicating with the interior of the second fan device and the waste gas treating area of the container; and a discharge adjusting valve assembled to the second linkage pipe.

3. The exhaust purification system as claimed in claim 2, wherein the container has a peripheral wall having a circular cross section; and the pump has an inlet pipe connected to the container and tangent to the circular cross section of the container.

4. The exhaust purification system as claimed in claim 3, wherein the centrifuge filter has a spring assembled in the container and disposed in the wastewater treating area.

5. The exhaust purification system as claimed in claim 4, wherein the centrifuge filter has a return line communicating with the wastewater treating area of the container and the pump;

a discharge line communicating with the wastewater treating area of the container; and a switch assembled to the discharge line; and the interior of the pump and the wastewater treating area of the container communicate with each other via the inlet pipe.

6. The exhaust purification system as claimed in claim 1, wherein the container has a peripheral wall having a circular cross section; and the pump has an inlet pipe connected to the container and tangent to the circular cross section of the container.

7. The exhaust purification system as claimed in claim 6, wherein the centrifuge filter has a spring assembled in the container and disposed in the wastewater treating area.

8. The exhaust purification system as claimed in claim 7, wherein the centrifuge filter has a return line communicating with the wastewater treating area of the container and the pump;

a discharge line communicating with the wastewater treating area of the container; and a switch assembled to the discharge line; and the interior of the pump and the wastewater treating area of the container communicate with each other via the inlet pipe.

* * * * *